(12) United States Patent
Wixey

(10) Patent No.: US 10,765,430 B2
(45) Date of Patent: Sep. 8, 2020

(54) KNIFE WITH MECHANICAL FUSE

(71) Applicant: Intuitive Surgical Operations, Inc., Sunnyvale, CA (US)

(72) Inventor: Matthew A. Wixey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 302 days.

(21) Appl. No.: 15/773,550

(22) PCT Filed: Oct. 28, 2016

(86) PCT No.: PCT/US2016/059297
§ 371 (c)(1),
(2) Date: May 3, 2018

(87) PCT Pub. No.: WO2017/079044
PCT Pub. Date: May 11, 2017

(65) Prior Publication Data
US 2018/0317916 A1 Nov. 8, 2018

Related U.S. Application Data

(60) Provisional application No. 62/251,838, filed on Nov. 6, 2015.

(51) Int. Cl.
| | |
|---|---|
| *A61B 17/072* | (2006.01) |
| *A61B 17/29* | (2006.01) |
| *A61B 17/068* | (2006.01) |
| *A61B 17/00* | (2006.01) |
| *A61B 90/00* | (2016.01) |
| *A61B 17/32* | (2006.01) |

(52) U.S. Cl.
CPC ...... *A61B 17/07207* (2013.01); *A61B 17/072* (2013.01); *A61B 17/068* (2013.01); *A61B 17/320016* (2013.01); *A61B 2017/00477* (2013.01); *A61B 2017/07214* (2013.01);
(Continued)

(58) Field of Classification Search
CPC ............... A61B 17/068; A61B 17/072; A61B 17/07207; A61B 17/320016;
(Continued)

(56) References Cited

U.S. PATENT DOCUMENTS

| | | | | |
|---|---|---|---|---|
| 5,389,104 A | * | 2/1995 | Hahnen | A61B 17/1608 606/174 |
| 5,700,270 A | * | 12/1997 | Peyser | A61B 17/1285 606/142 |

(Continued)

OTHER PUBLICATIONS

International Search Report and Written Opinion for Application No. PCT/US2016/059297, dated Jan. 17, 2017, 10 pages.
(Continued)

*Primary Examiner* — Scott A Smith
(74) *Attorney, Agent, or Firm* — Kilpatrick Townsend & Stockton LLP

(57) ABSTRACT

A knife member that can have a blade portion configured operation within a surgical stapling device. A first frame portion can extend from the blade portion to a first connection portion. A second frame portion can extend from the first frame portion to a second connection portion. At least one of the first and second frame portions can include a fused portion. The fused portion can be configured to fail when a predetermined amount of force is applied to the fused portion.

21 Claims, 13 Drawing Sheets

(52) U.S. Cl.
CPC ............... *A61B 2017/07271* (2013.01); *A61B 2017/07278* (2013.01); *A61B 2017/07285* (2013.01); *A61B 2017/2927* (2013.01); *A61B 2017/2945* (2013.01); *A61B 2090/037* (2016.02)

(58) Field of Classification Search
CPC ...... A61B 17/1114; A61B 2017/00477; A61B 2017/00685; A61B 2017/07271; A61B 2017/07278; A61B 2017/07285; A61B 2017/00862; A61B 2017/2945; A61B 2090/037
USPC .............. 227/19, 175.1, 176.1, 175.2, 180.1; 606/1, 139, 167, 170, 219
See application file for complete search history.

(56) References Cited

U.S. PATENT DOCUMENTS

| | | |
|---|---|---|
| 5,797,938 A | 8/1998 | Paraschac et al. |
| 5,800,449 A | 9/1998 | Wales |
| 7,722,607 B2 * | 5/2010 | Dumbauld ......... A61B 18/1445 606/45 |
| 9,055,941 B2 * | 6/2015 | Schmid ............ A61B 17/00491 |
| 9,272,406 B2 * | 3/2016 | Aronhalt ............ A61B 17/0643 |
| 9,320,523 B2 * | 4/2016 | Shelton, IV ......... A61B 17/068 |
| 9,386,984 B2 * | 7/2016 | Aronhalt .......... A61B 17/07207 |
| 9,585,657 B2 * | 3/2017 | Shelton, IV ....... A61B 17/1155 |
| 9,814,462 B2 * | 11/2017 | Woodard, Jr. ....... A61B 17/072 |
| 9,844,374 B2 * | 12/2017 | Lytle, IV ............... A61B 90/03 |
| 9,962,161 B2 * | 5/2018 | Scheib ............ A61B 17/07292 |
| 2004/0199181 A1 | 10/2004 | Knodel et al. |
| 2007/0114261 A1 | 5/2007 | Ortiz et al. |
| 2014/0239048 A1 | 8/2014 | Racenet et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

KNIFE WITH MECHANICAL FUSE

CROSS REFERENCE TO RELATED APPLICATIONS

The present application is a U.S. National Stage application of PCT/US2016/059297 filed Oct. 28, 2016, which claims priority to, and the benefit of, U.S. Provisional Patent Application 62/251,838 filed Nov. 6, 2015, the full disclosures which are incorporated herein by reference in their entirety for all purposes.

BACKGROUND OF THE INVENTION

Surgical clamping and cutting instruments (e.g., linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting instruments, including known surgical staplers, have opposing jaws that clamp tissue and an articulated knife to cut the clamped tissue.

In the case of telesurgical controlled instruments, surgical clamping and cutting instruments are often deployed into restrictive body cavities (e.g., through a cannula to inside the pelvis). Accordingly, it is desirable for a surgical clamping and cutting instrument to be both compact and maneuverable for best access to and visibility of the surgical site.

Surgical clamping and cutting instruments can sometimes fail to fully actuate (e.g., due to a hard obstacle blocking the knife path). In such an event, it is desirable that the knife blade not be in a position that may represent a hazard with respect to removal of the surgical instrument from the surgical site. Known surgical clamping and cutting instruments, however, may fail to avoid the potential knife hazard and at the same time be compact and maneuverable.

Thus, there is believed to be a need for improved surgical clamping and cutting instruments and related methods. Such surgical clamping and cutting instruments should be compact and maneuverable, and employ a knife that does not represent a hazard with respect to removal of the surgical instrument from the surgical site when the surgical instrument fails to fully actuate.

BRIEF SUMMARY OF THE INVENTION

Some embodiments of the invention relate to a knife member. The knife member can have a blade portion configured for operation within a surgical stapling device. A first frame portion can extend from the blade portion to a first connection portion. A second frame portion can extend from the first frame portion to a second connection portion. At least one frame portion of the first frame portion and second frame portion can include a fused portion, and be terms a fused frame portion. The fused portion can be configured to fail when a predetermined amount of force is applied to the fused portion.

Some embodiments of the invention a surgical stapling cartridge. The cartridge can be configured to removably attach to a jaw of an end effector and have a plurality of staples arranged along a slot. A drive member can be configured to travel along the slot. A knife member can be configured to be carried by the drive member and have a blade portion that extends above the slot. The knife member can have a fused portion configured to fail and recede beneath the slot when a predetermined amount of force is applied to the fused portion.

In some embodiments, the fused portion can be a notched portion.

In some embodiments, the fused portion can be a relatively thin section relative to part or all of the remainder of the first frame portion or second frame portion.

In some embodiments, the fused portion can fail by fracturing.

In some embodiments, the fused portion can fail by bending.

In some embodiments, the first frame portion or second frame portion can have an opening.

In some embodiments, the fused portion can be proximate to the opening.

In some embodiments, the first frame portion or second frame portion can include a first strut and a second strut, with the first strut being separated from the second strut by the opening.

In some embodiments, the fused portion is a notched portion of the first strut.

In some embodiments, the second frame portion can be an elongated strut.

In some embodiments, the elongated strut can be configured to elastically deform into the fused portion.

In some embodiments, the first frame portion and the second frame portion can have a laminated construction including a first sheet and a second sheet.

In some embodiments, the blade portion and the fused portion can be located on the second sheet.

DETAILED DESCRIPTION OF THE INVENTION

Cutting implements of surgical stapling and cutting devices can jam while actively cutting tissue. Jamming can occur due to a jamming substance (e.g., bone, tissue, and/or staples) impinging the cutting implement and bringing it to a halt. Often, this situation cannot be easily remedied and requires physical intrusion into the sterile field to physically remove the associated stapling device. Embodiments of a knife member disclosed herein may address these situations by incorporating one or more fused portions configured to control the mechanical failure of the knife member. Such fused portions can fail in a mode to cause the knife blade (also called the cutting blade) to be freed from the jamming substance. A fused portion can be configured to fail by breaking and/or bending one or more portions of the knife member. For example, the fused portion may be configured to fail by material fracture, by plastic deformation, a combination thereof, etc. under particular loading conditions. As another example, the fused portion may be configured to cause the knife member to fail in a particular configuration or in a particular way that reduces jamming, increases retention of the knife member after breakage, improves patient safety, a combination thereof, and the like. The fused portion is termed "fused" because it may be configured to act like a mechanical analog of an electrical fuse, and be designed fail under particular loading conditions.

Figure 1:
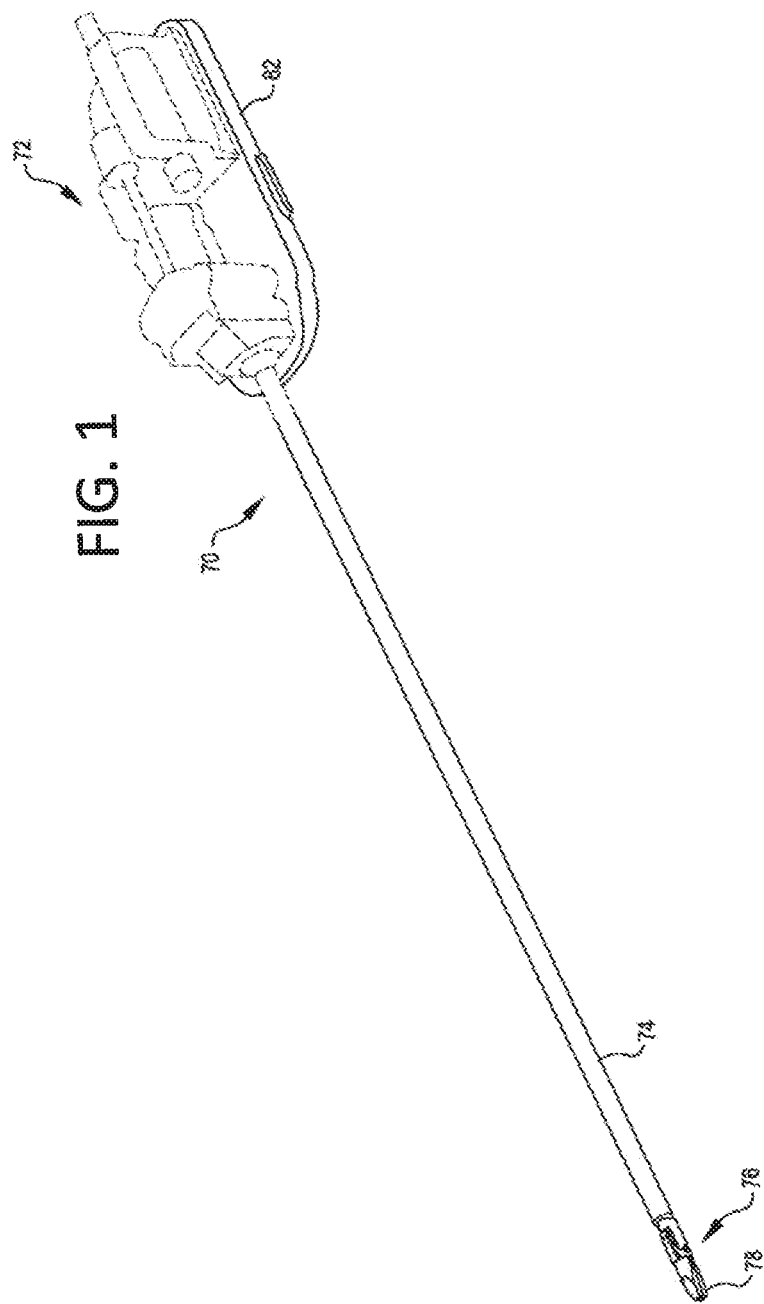
FIG. 1 is a perspective view of a robotic surgery tool that includes an end effector having opposed clamping jaws, in accordance with some embodiments.

FIG. 1 shows a surgical tool 70 that includes a proximal chassis 72 that can be coupled with an adapter 82, an instrument shaft 74, and a distal end effector 76 having a jaw 78 that can be articulated to grip a patient tissue. The proximal chassis includes input couplers that may interface with and be driven by corresponding output couplers of a telesurgical surgery system, such as the system disclosed within Pub. No. US20140183244A1, which is incorporated by reference herein. The input couplers are drivingly coupled with drive shafts that are disposed within the instrument shaft 74. The drive shafts are drivingly coupled with the end effector 76.

Figure 2:
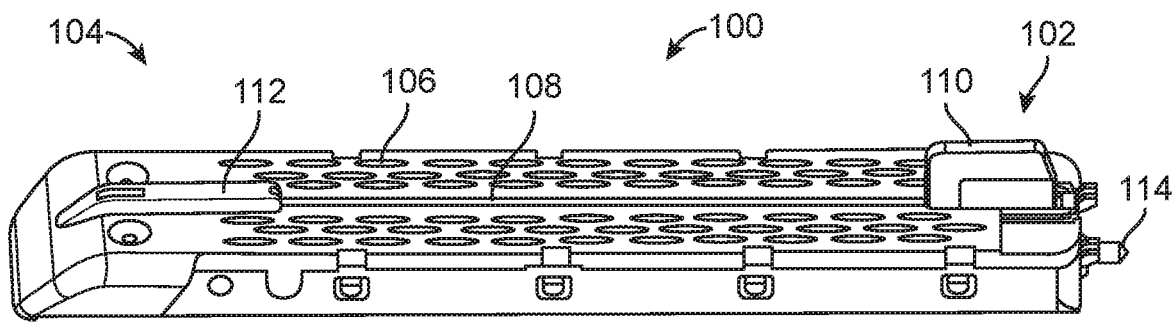
FIG. 2 is a perspective view of a demountably attachable cartridge of a linear stapling and cutting surgical instrument having six rows of staples, in accordance with some embodiments.
Figure 3:
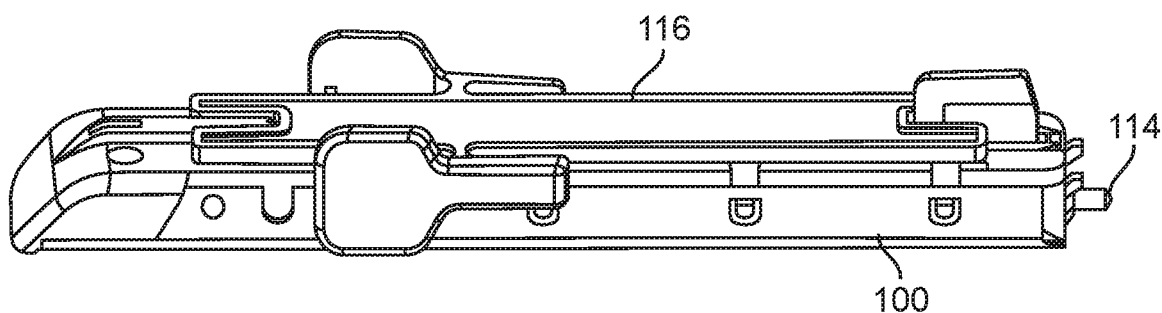
FIG. 3 is a perspective view of the cartridge of FIG. 2 and an attached staple retainer, in accordance with some embodiments.

FIG. 2 shows a demountably attachable cartridge 100 of a linear stapling and cutting surgical instrument, in accordance with many embodiments. The cartridge 100 is configured to removably attach to a jaw of an end effector. The cartridge has a proximal end 102 that is attached to the jaw of the end effector and a distal end 104 disposed at a corresponding distal end of the jaw of the end effector. The cartridge 100 includes six rows of staple openings 106, a longitudinal slot 108, a proximal knife garage 110, a distal knife garage 112, and a rotational input 114. In many embodiments, a staple is disposed in each of the staple openings for deployment there from. The longitudinal slot 108 accommodates a cutting blade of a knife member (not shown) extending there from as the knife member is moved from the proximal knife garage 110 to the distal knife garage 112. In operation, the staples are deployed starting at the cartridge proximal end 102 and proceeding to the cartridge distal end 104. The cutting blade is moved to trail the stapling of the tissue to ensure that only fully stapled tissue is cut. FIG. 3 shows the cartridge 100 with an attached staple retainer 116, which is removed prior to using the cartridge 100.

Figure 4:
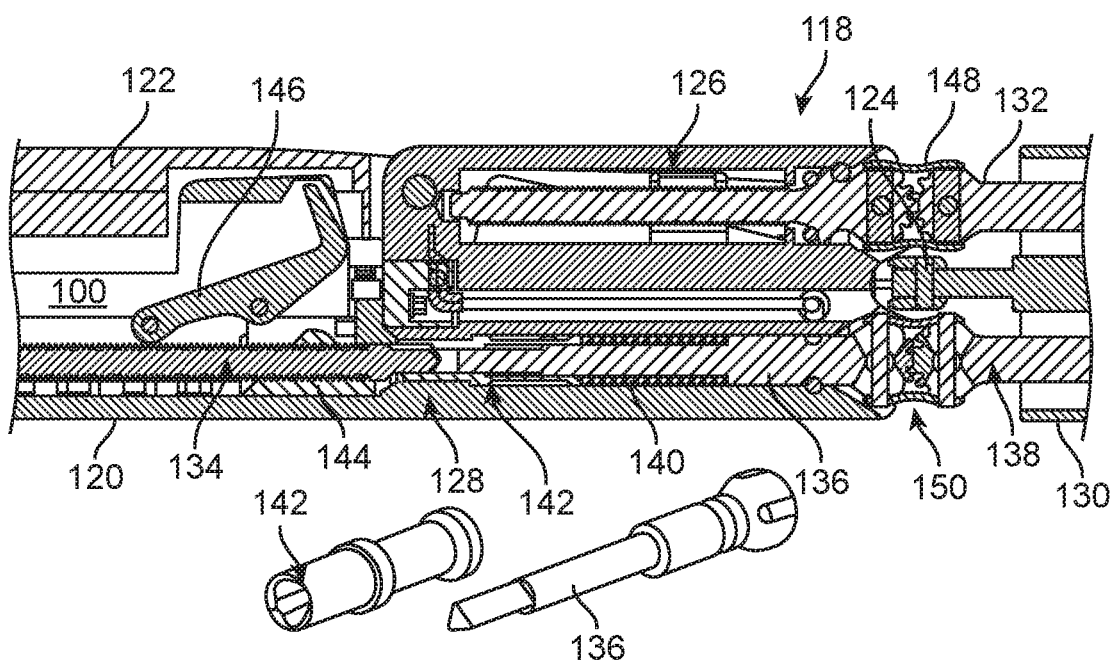
FIG. 4 is a cross-sectional view showing attachment details between the cartridge of FIG. 2 and an end effector assembly, in accordance with some embodiments.

FIG. 4 is a cross-sectional view showing details of the attachment of the cartridge 100 to an end effector 118, in accordance with many embodiments. The end effector 118 includes a lower jaw 120, an upper jaw 122, a two degree of freedom wrist 124, a rotationally-driven clamping mechanism 126, and a spring loaded coupling 128. The lower jaw 120 is configured to accommodate and support the cartridge 100, as well as position the cartridge 100 relative to the spring loaded coupling 128. The upper jaw 122 is pivotally coupled with the lower jaw 120 to articulate relative to the lower jaw 120 to clamp tissue. The upper jaw 122 includes staple forming recesses configured and positioned relative to the staple openings 106 to form the staples into a "B" shape upon deployment of the staples.

The two degree of freedom wrist 124 provides for attachment of the end effector 118 to an elongated instrument shaft 130 for articulation of the end effector 118 about two orthogonal axes relative to the instrument shaft 130. The rotationally-driven clamping mechanism 126 actuates the upper jaw 122 relative to the lower jaw 120 to securely clamp tissue between the upper and lower jaws. The clamping mechanism 126 is rotationally driven by a first drive shaft 132 disposed internal to the instrument shaft 130.

The spring-loaded coupling 128 rotationally couples a lead screw 134 of the cartridge 100 with an extension shaft 136, which is driven by a second drive shaft 138 disposed internal to the instrument shaft 130. The spring-loaded coupling 128 includes a coil spring 140 and a coupling fitting 142. In the embodiment shown, the coupling fitting 142 employs a three-lobe spline receptacle that interfaces with three-sided external surfaces of the rotational input 114 and of the extension shaft 136. The spring-loaded coupling 142 accommodates angular misalignment of the three-lobe spline that might occur when cartridge 100 is installed into end effector 118. The spring-loaded coupling 142 fully engages the three-lobe spline when rotated into angular alignment. Rotation of the lead screw 134 is used to translate a drive member 144 of the cartridge 100. The resulting motion of the drive member 144 is used to deploy the staples and to distally advance a knife member 146 of the cartridge 100 to cut the clamped tissue down the center of the rows of deployed staples.

The end effector 118 includes a first universal joint assembly 148 and a second universal joint assembly 150. The first universal joint assembly 148 rotationally couples the clamping mechanism 126 to the first drive shaft 132. The second universal joint assembly 150 rotationally couples the extension shaft 136 to the second drive shaft 138. Each of the first and second universal joint assemblies 148, 150 is configured to transmit torque through a range of angles suitable to the range of Pitch and Yaw of the end effector 118 relative to the instrument shaft 130. The first and second drive shafts 132, 138 are disposed offset to the centerline of the instrument shaft 130, which may be independently rotated.

Figure 5:
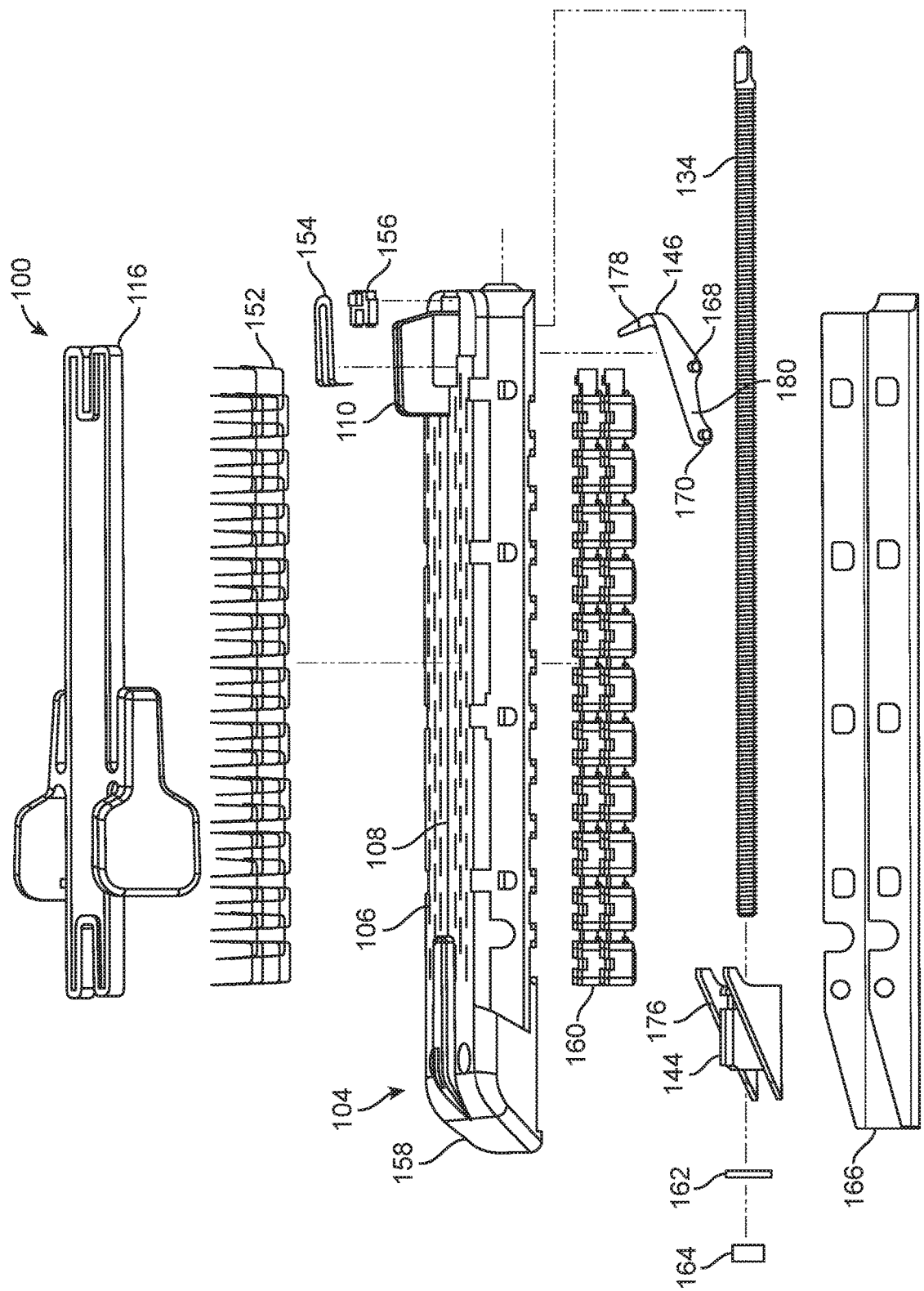
FIG. 5 is an exploded perspective view illustrating components of the cartridge of FIG. 2.

FIG. 5 is an exploded perspective view illustrating components of the cartridge 100. The illustrated components include the retainer 116, 66 staples 152, a printed circuit assembly (PCA) spring 154, a PCA 156, a cartridge body 158, 22 staple pushers 160, the knife member 146, the lead screw 134, the drive member 144, a thrust washer 162, a lead screw nut 164, and a cover 166. The cartridge body 158 has the 66 staple openings 106 arranged in 6 rows, with 3 rows of the staple openings 106 being disposed on each side of the longitudinal slot 108. The retainer 116 is removably attachable to the cartridge 100 and covers the staple openings 106 to retain the staples 152 prior to use of the cartridge 100. The staple pushers 160 interface with the staples 152 and slidingly interface with the cartridge body 158. Motion of the drive member 144 along the lead screw 134 results in engagement of the staple pushers 160 by distally-facing ramp surfaces 176 of the drive member 144 to drive the staple pushers 160 up relative to the cartridge body 158 to deploy the staples 152 as the drive member 144 moves towards the distal end 104. The knife member 146 includes proximal protrusions 168 and distal protrusions 170. The cover 166 is attached to the cartridge body 158.

Figure 6:
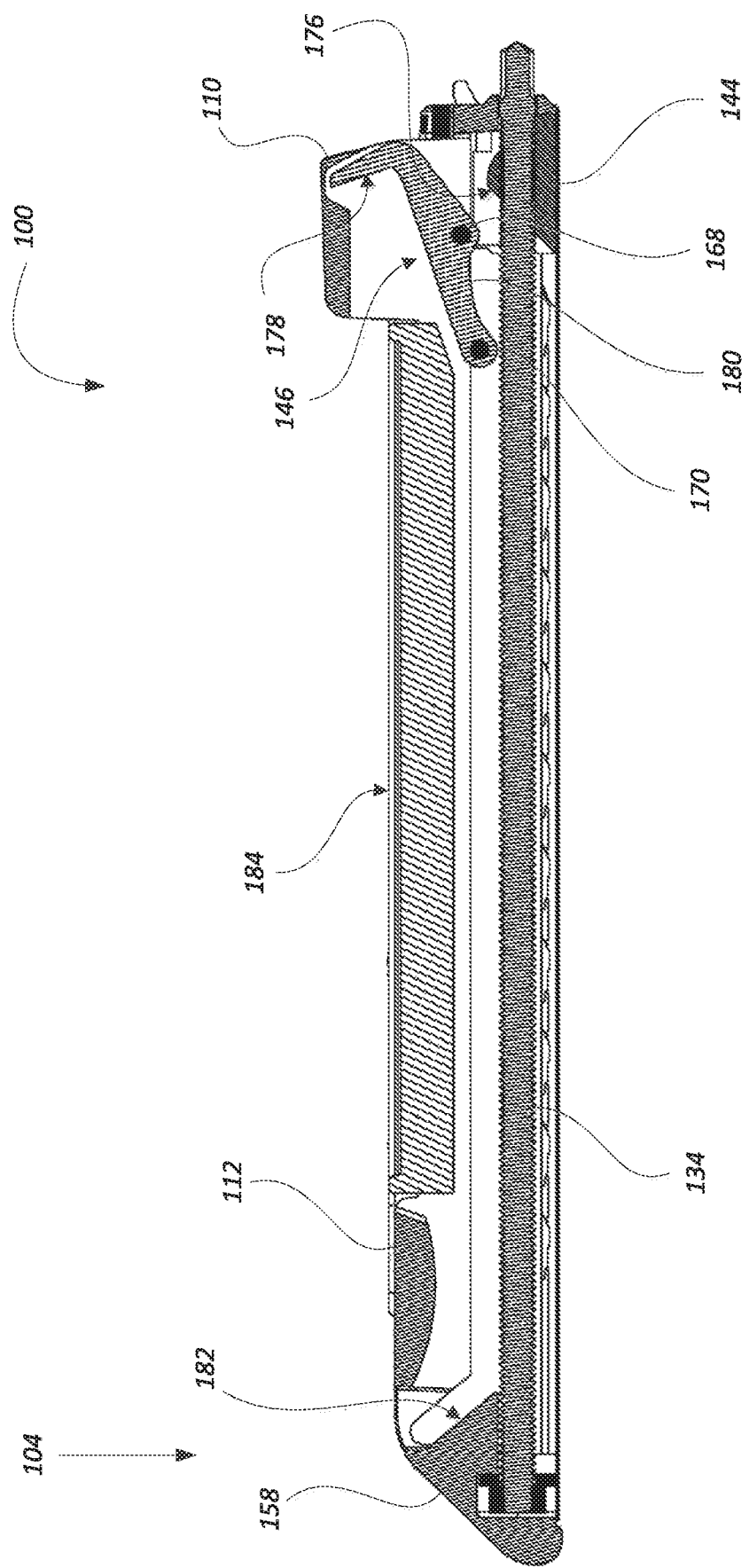
FIG. 6 is a cross-sectional view of a demountably attachable cartridge of a linear stapling and cutting surgical instrument, in accordance with some embodiments.

FIG. 6 illustrates components of the cartridge 100 related to the actuation of the knife member 146 from a starting position (illustrated) in which the knife member 146 is shielded by the proximal garage 110 to an ending position (not illustrated) in which the knife member 146 is shielded by the distal garage 112. The lead screw 134 is mounted for rotation relative to the cartridge body 158 and extends along the length of the cartridge body 158. The drive member 144 is internally threaded and is coupled with the lead screw 134 and slidably mounted in the cartridge body 158 for translation along the lead screw 134 in response to rotation of the lead screw 134. The drive member 144 includes one or more distally-facing ramps 176 configured to engage the staple pushers 160 as the drive member 144 is advanced toward the distal end 104 of the cartridge body 100. The knife member 146 includes a knife blade 178 (also called cutting blade 178), the body portion 180, the proximal protrusions 168 extending from opposite sides of the body portion 180, and the proximal protrusions 170 also extending from opposite sides of the body portion 180. As will be described in more detail below, when the drive member 144 is advanced distally from its illustrated starting position, the knife member 146 remains stationary relative to the cartridge body 158 until the drive member 144 contacts the distal protrusions 170 by which the knife member 146 is then driven distally by the drive member 144. Near the end of the distal travel of the drive member 144, the distal end of the knife member 146 is driven along a cam surface 182 of the cartridge body 158, thereby raising the distal end of the knife member 146 to lower the knife blade 178 below an upper surface 184 of the cartridge body 158 and into the distal garage 112. The knife member body portion 180 is constrained by opposing surfaces of the cartridge body 158 that define the longitudinal slot 108. The knife proximal and distal protrusions 168, 170 extend from opposite sides of the knife member body portion 180 beyond the width of the longitudinal slot 108, thereby serving to constrain the knife member 146 vertically relative to the cartridge body 158 and the drive member 144.

Figure 7A:
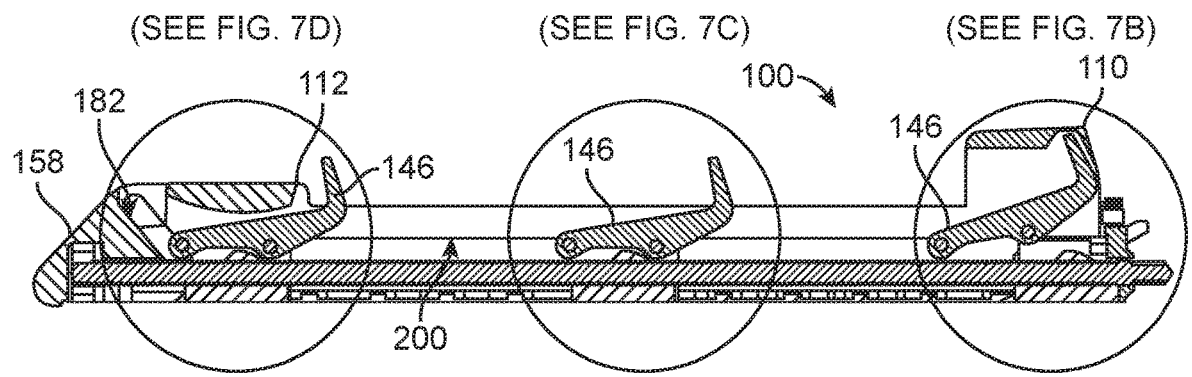
FIG. 7A illustrates the actuation of the knife member of the cartridge of FIG. 7.

FIGS. 7A through 7D illustrate the interaction of components of the cartridge 100 during the actuation of the knife member 146 from its starting position in the proximal garage 110 to its final position in the distal garage 112. FIG. 7A shows three different positions of the knife member 146 relative to the cartridge body 158, specifically a starting proximal-most position, an intermediate position, and a distal position just before the distal end of the knife member 146 is driven up the cartridge body cam surface 182.

Figure 7B:
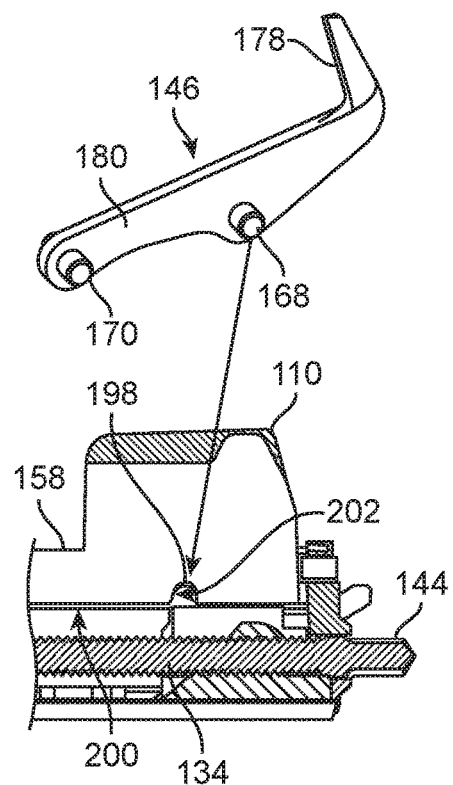
FIG. 7B shows a housing receptacle that receives a protrusion of the knife member to restrain the knife member from moving distally during a movement of the drive member distally, in accordance with some embodiments.

As shown in FIGS. 7A and 7B, in the starting proximal-most position, the drive member 144 is positioned at the proximal end of the lead screw 134 and the knife member proximal protrusions 168 are disposed within receptacles 198 in the cartridge body 158. The drive member upper surfaces 194 interface with the knife member proximal protrusions 168 to retain the proximal protrusions 168 in the cartridge body receptacles 198, thereby securing engagement between the proximal protrusions 168 and the cartridge body receptacles 198. The knife member distal protrusions 170 and the distal end of the knife are trapped between a central cavity ceiling 200 of the cartridge body 158 and the lead screw 134 and the knife member body portion 180 is disposed within the longitudinal slot 108, thereby restraining the knife member 146 in a substantially fixed position and orientation relative to the cartridge body 158.

From the starting proximal-most position, rotation of the lead screw 134 drives the drive member 144 distally along the lead screw 134. Throughout a starting "lost-motion" portion of the distal motion of the drive member 144 along the lead screw 134, the proximal protrusions 168 remain trapped in the cartridge body receptacles 198 by the drive member upper surfaces 194. When the drive member 144 has moved distally to a point where the drive member distal surfaces 196 contact the knife member distal protrusions 170, the drive member proximal receptacles 192 are disposed below the cartridge body receptacles 198, thereby permitting the knife member 146 to rotate to transfer the proximal protrusions 168 from the cartridge body receptacles 198 to the drive member proximal receptacles 192. To facilitate this transfer, a distal surface 202 of the cartridge body receptacles 198 is sloped as illustrated to enhance the transfer by imparting a downward force component on the proximal protrusions 168 as the knife member distal surfaces 196 drive the knife member 146 distally via contact with the knife member distal protrusions 170.

Figure 7C:
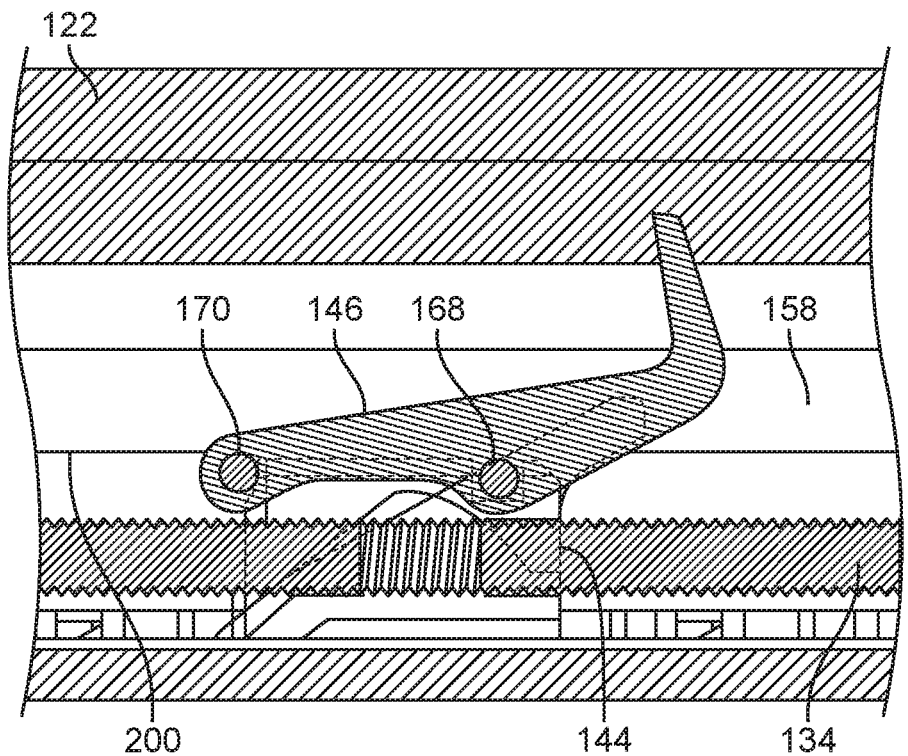
FIG. 7C shows the knife member coupled with the drive member while the drive member drives the knife member distally, in accordance with some embodiments.

FIG. 7C illustrates interaction between the drive member 144, the knife member 146, and the cartridge body 158 following the "lost motion" portion of the distal motion of the drive member 144 along the lead screw 134. After the drive member distal surfaces 196 come into contact with the knife member distal protrusions 170 causing the knife member 146 to rotate to transfer the proximal protrusions 168 into the drive member proximal receptacles 192, continued rotation of the lead screw 134 results in continued distal motion of the drive member 144 and corresponding distal motion of the knife member 146. During this continued distal motion, the knife member 146 is constrained by both the drive member distal protrusions 170 interaction with the ceiling 200 of the cartridge body 158 and the knife member body portion 180 interaction within the longitudinal slot 108 of the cartridge body 158.

Figure 7D:
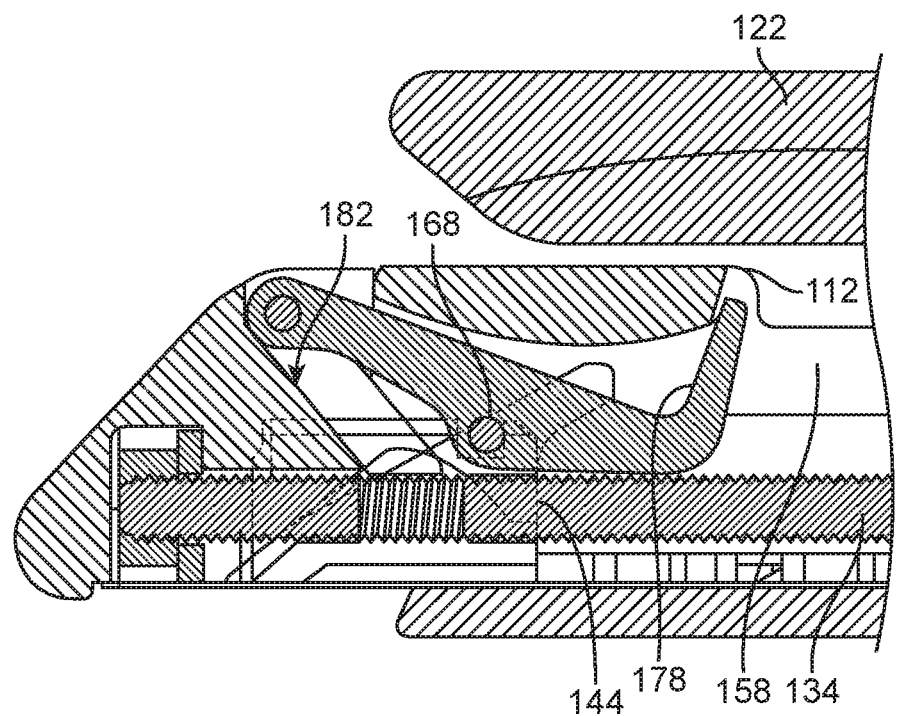
FIG. 7D shows the knife member at the end of the actuation stroke after the distal end of the knife member has been driven along a cam surface of the housing to raise the distal end of the knife to lower the knife blade of the knife into the housing, in accordance with some embodiments.

FIGS. 7A and 7D illustrate interaction between the drive member 144, the knife member 146, and the cartridge body 158 (particularly the cam surface 182 of the cartridge body 158) during a terminal portion of the distal motion of the drive member 144 along the lead screw 134. As the drive member 144 is advanced distally near the end of its travel along the lead screw 134, the distal end of the knife member 146 comes into contact with the cam surface 182 and is subsequently driven along the cam surface 182 until reaching the ending distal-most position illustrated in FIG. 7D in which the drive member 144 has reached the end of its travel along the lead screw 134. As a result of the distal end of the knife member 146 being driven along the upward sloping cam surface 182, the knife member 146 rotates approximately around the knife member proximal protrusions 168, thereby lowering the knife blade 178 into the distal garage 112.

In some cases, the knife member 146 can jam in the modes shown at FIGS. 7C-7D, which are modes where the knife member 146 can actively cut tissue. Jamming can occur due to a jamming substance (e.g., bone, tissue, and/or staples) impinging the knife member 146 and bringing it to a halt. Often, this situation cannot be easily remedied and requires physical intrusion into the sterile field to physically remove the associated stapling device. Embodiments of the knife member 146 may address these situations by incorporating a fused portion, which is configured to fail in a mode where the knife blade 178 is placed below the longitudinal slot 108 and freed from the jamming substance. The fused portion can be configured to fail by breaking and/or bending one or more portions of the knife member 146.

Figure 8A:
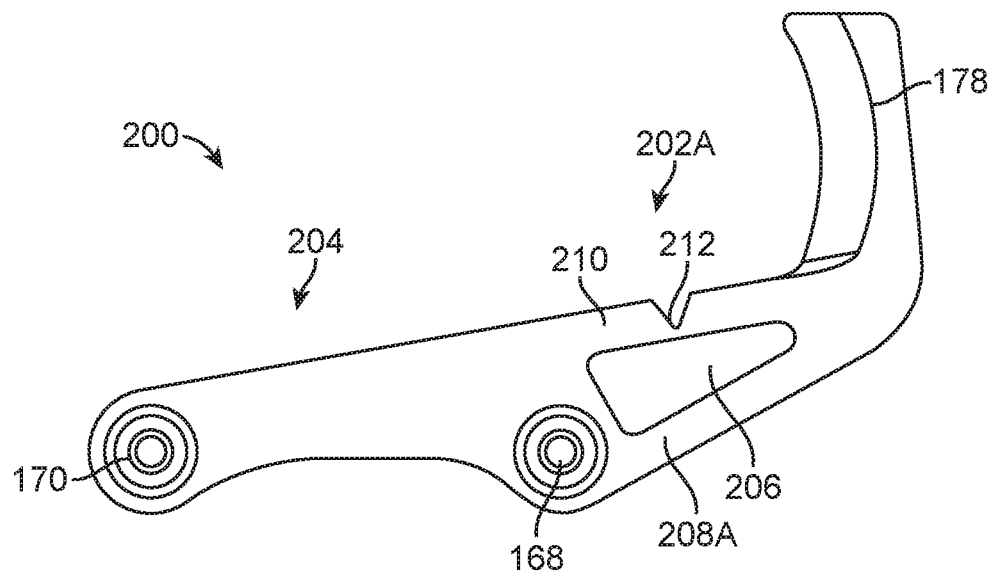
FIGS. 8A-8C show side views of knife members having mechanical fuses, in accordance with some embodiments.

FIG. 8A shows a knife member 200 having a first frame portion 202A spanning approximately between knife blade 178 and proximal protrusion 168. The knife member 200 also includes a second frame portion 204 spanning approximately between the first frame portion 202 and distal protrusion 170. Here, the first frame portion 202A includes an opening 206 defining a spatial separation between a lower strut 208A and an upper strut 210. Upper strut 210 includes a fused portion 212, which can be configured as a notched or thinned portion having a reduced thickness when compared to another part of the upper strut 210, such as a portion near or adjacent to the fused portion 212. Thus, the first frame portion 202A comprises the fused portion 212 and can be termed a fused frame portion. In some embodiments, the fused portion 212 is the thinnest portion of the upper strut 210.

Figure 8B:
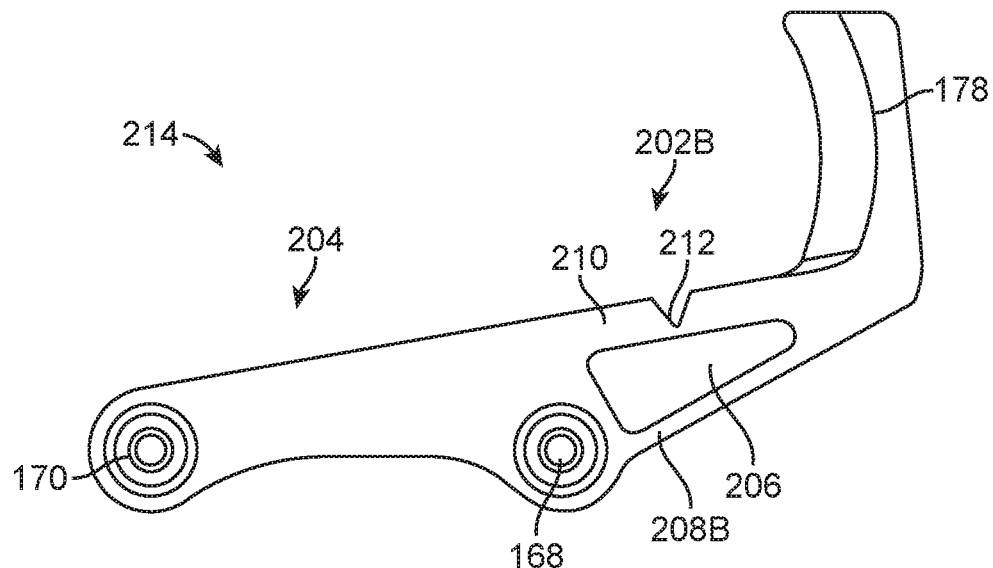

In use, distal movement of the knife blade 178 will apply torque to the proximal protrusion 168 and thereby place the upper strut 210 in tension. Jamming of the device increases this tension greatly as the lead screw 134 continuously tries to drive the drive member 144 forward against the jam. Once this tension meets a predetermined amount of force, the fused portion will fracture. After the fracture occurs, the knife blade 178 continually applies torque to proximal protrusion 168, which then causes the lower strut to bend downward, and thereby place the knife blade underneath the longitudinal slot 108 and alleviating the jam. The thickness of the lower strut 208A can be tuned mechanically for failure force by changes in geometry or material. The embodiment of a knife member 214 shown at FIG. 8B is an example of a geometric change. The knife member 214 is identical to the knife member 200 except that the knife member 214 comprises a first frame portion 202B with a lower strut 208B that is thinner than the lower strut 208A shown at FIG. 8A. Thus, the knife member 2014 will bend at a lower threshold of force in comparison to the knife member 200. Other embodiments may tune mechanically for failure force by adjusting the geometry or material of one or more parts of the knife member.

Figure 8C:
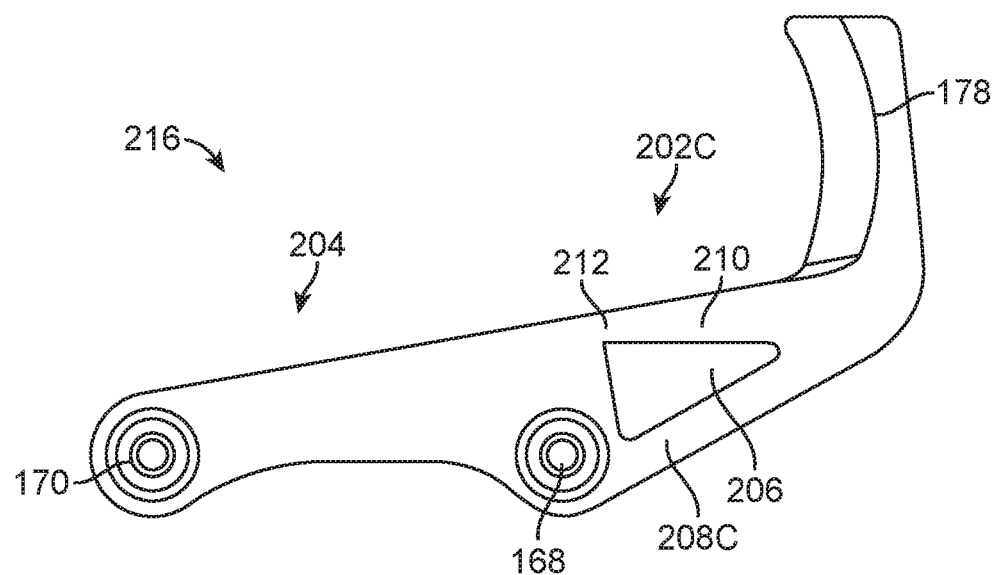

FIG. 8C shows a knife member 216 similar to the knife member 200 depicted at FIG. 8A. However, the first frame member 202C comprises a fused portion 212C that does not include a notched portion. Instead, the fused portion 212C comprises a thinner section of material along the upper strut 210 that is thinner relative to another part of the upper strut 210. In some embodiments, the fused portion 212 comprises the thinnest section of material of the upper strut 210. Hence, failure will generally occur at the fused portion 212 due to it being the weakest portion of the first frame portion 202C.

Figure 8D:
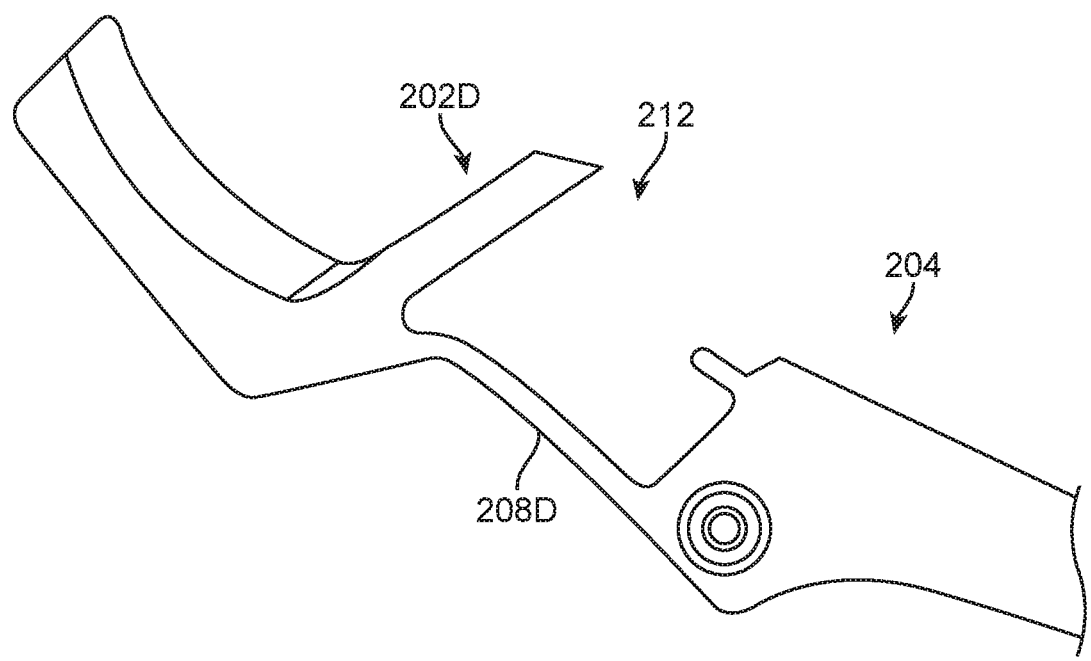
FIG. 8D shows a failure mode of knife member having a mechanical fuse, in accordance with some embodiments.

FIG. 8D shows a typical failure mode of the embodiments shown at FIGS. 8A-8C. Here, the fused portion 212 has fractured within the first frame portion (e.g. first frame portions 202A, 202B, 202C). However, the first frame portion 202A, 202B, or 202C and the second frame portion 204 remain linked by the lower strut 208A, 208B, or 208C, respectively. In the failure shown in FIG. 8D, the lower strut 208D is now significantly bent.

Figure 9A:
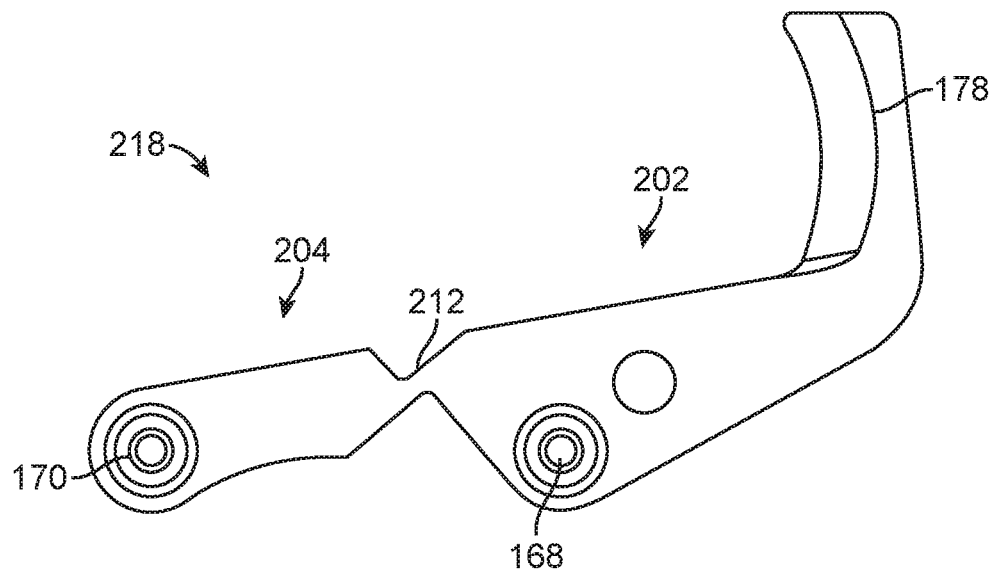
FIGS. 9A-9C show side views of knife members having mechanical fuses, in accordance with some embodiments.

FIG. 9A shows a knife member 218 having the fused portion 212 located at the second frame portion 204. The fused portion 212 is configured as a thinned portion of material of the second frame portion 204, and the fused portion is thinner relative to another part of the second frame portion 204, such as a portion near or adjacent to the fused portion 212. Hence, failure will occur at the fused portion 212 due to it being the weakest portion of the second frame portion 204. In use, distal movement of the knife blade 178 will apply torque to the proximal protrusion 168 and thereby place the second frame portion 204 in tension. Jamming increases this tension greatly as the lead screw 134 continuously tries to drive the drive member 144 forward against the jam. Once this tension meets a predetermined amount of force, the fused portion 212 will fracture or elastically deform to a great degree, essentially breaking the knife member 218 into two parts. After the failure occurs the knife blade 178 continually applies torque to proximal protrusion 168, which then causes the knife blade 178 and first frame portion 202 to rotate clockwise, and thereby place the knife blade 178 underneath the longitudinal slot 108 and alleviate the jam.

Figure 9B:
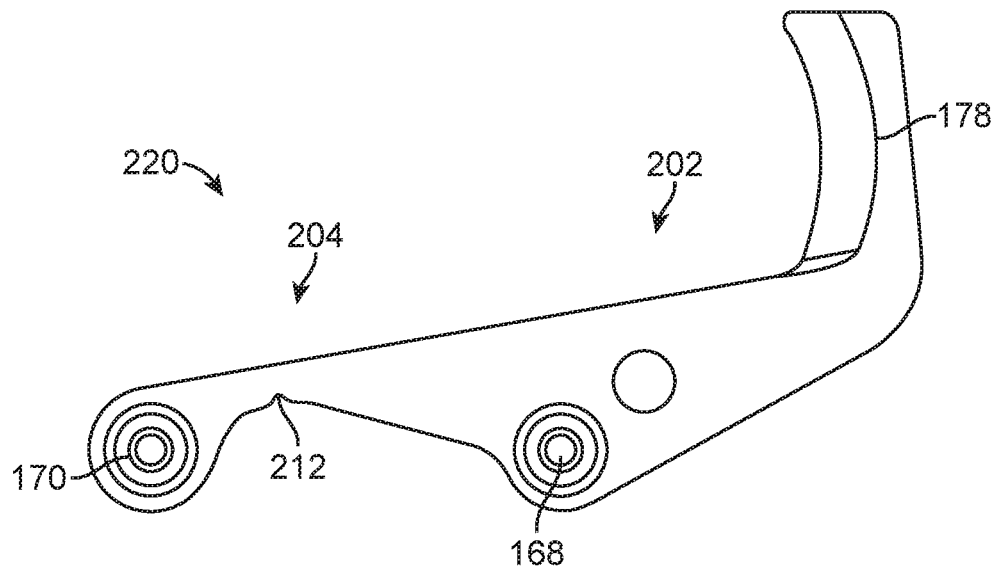

FIG. 9B also shows a knife member 220 having the fused portion 212 located at the second frame portion 204, and such a second frame portion 204 can be termed a fused frame portion. Here, the fused portion 212 is defined by a notched portion, which will fracture in response to sufficient force because it has the smallest cross-sectional area of the second frame portion 204 and is a location of high stress concentration when knife member 220 is jammed. In use, the failure mode will be similar to that of knife member 218, with the knife member 220 breaking into two separate parts.

Figure 9C:
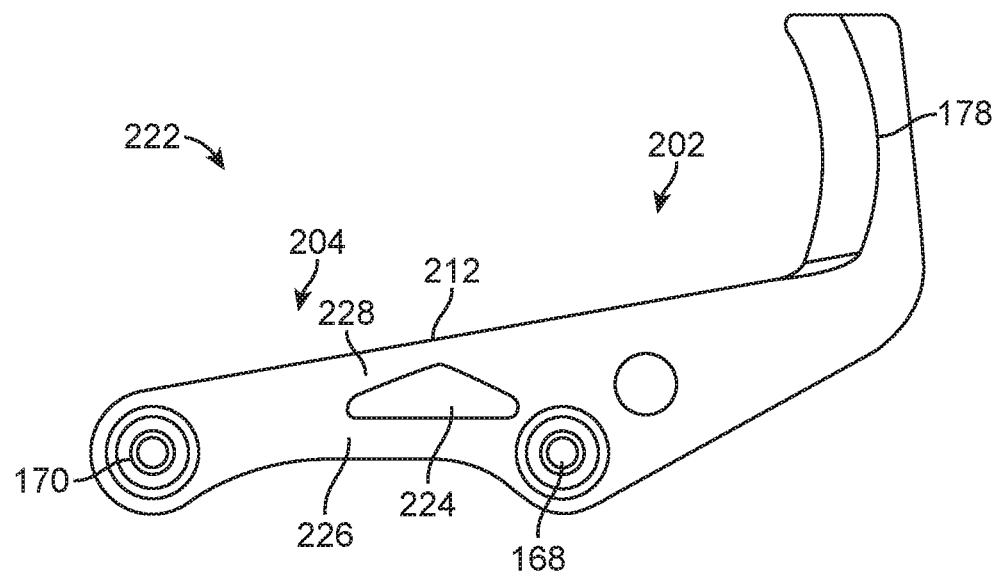

FIG. 9C shows a knife member 222 having the fused portion 212 located at the second frame portion 204. Here, the second frame portion 204 includes an opening 224 defining a spatial separation between a lower strut 226 and an upper strut 228. Upper strut 228 includes the fused portion 212, which here is configured as a notched or thinned portion having a reduced thickness relative to another portion of the upper strut 228, such as a portion near or adjacent to the fused portion 212. In use, the fused portion 204 will fracture or elastically deform to a great degree. However, unlike the knife member 218 shown at FIG. 9A, the knife member 222 will not break into two parts because the lower strut 226 bends, but remains connected between the first frame portion 202 and the second frame portion 204.

Figure 9D:
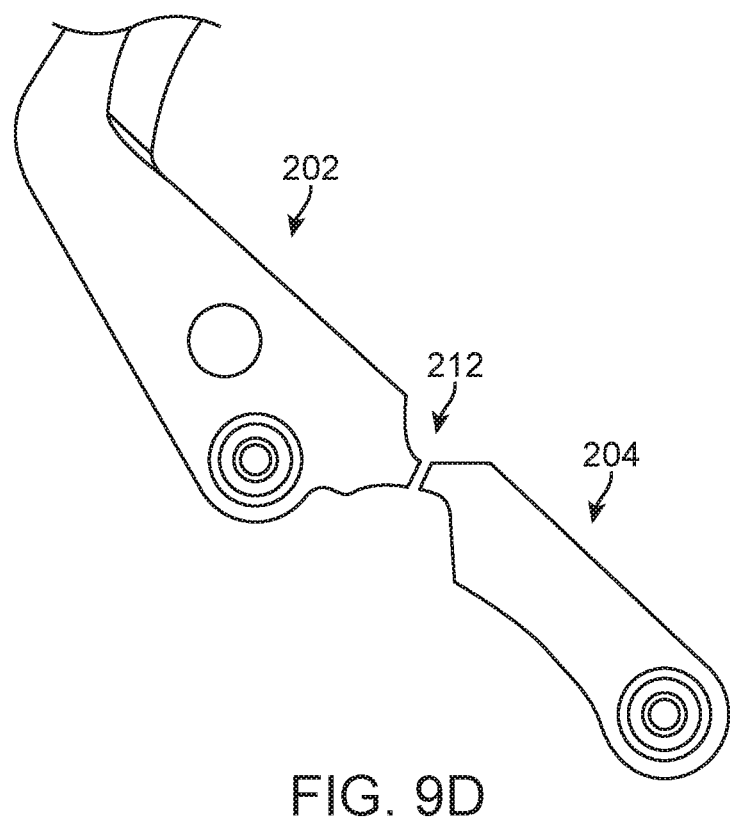
FIG. 9D shows a failure mode of a knife member having a mechanical fuse, in accordance with some embodiments.

FIG. 9D shows a typical failure mode of the embodiments shown at FIGS. 9A and 9B. Here, the fused portion has fractured within the second frame portion 204, separating the first frame portion 202 from the second frame portion 204.

Figure 10A:
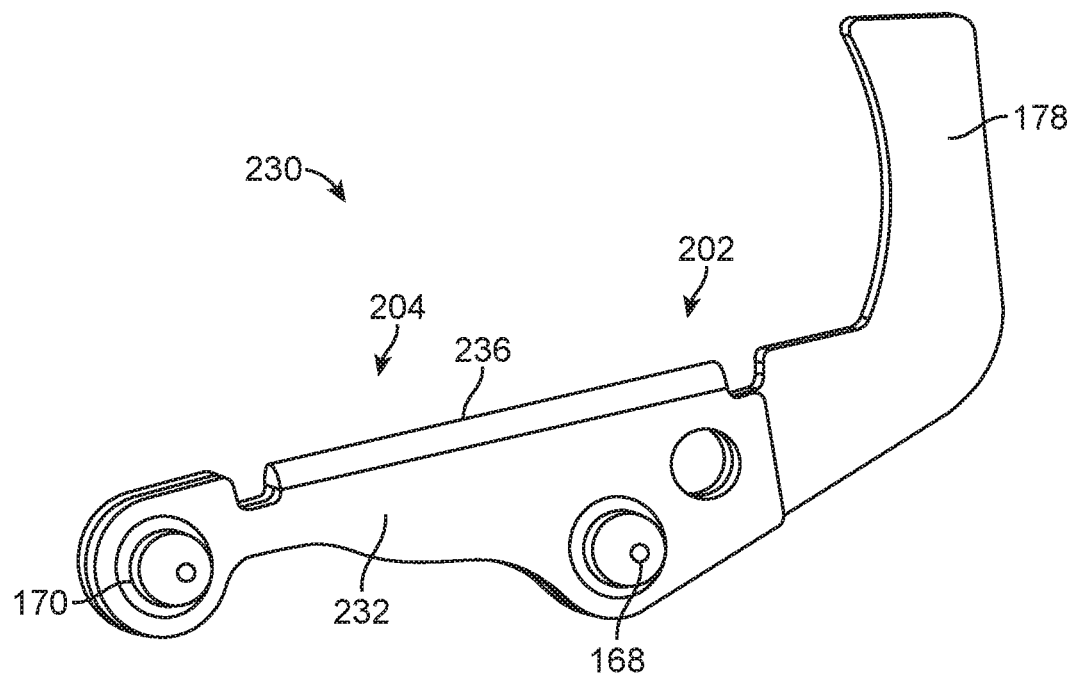
FIGS. 10A-10C show perspective views of knife members having a laminate construction and mechanical fuses, in accordance with some embodiments.
Figure 10B:
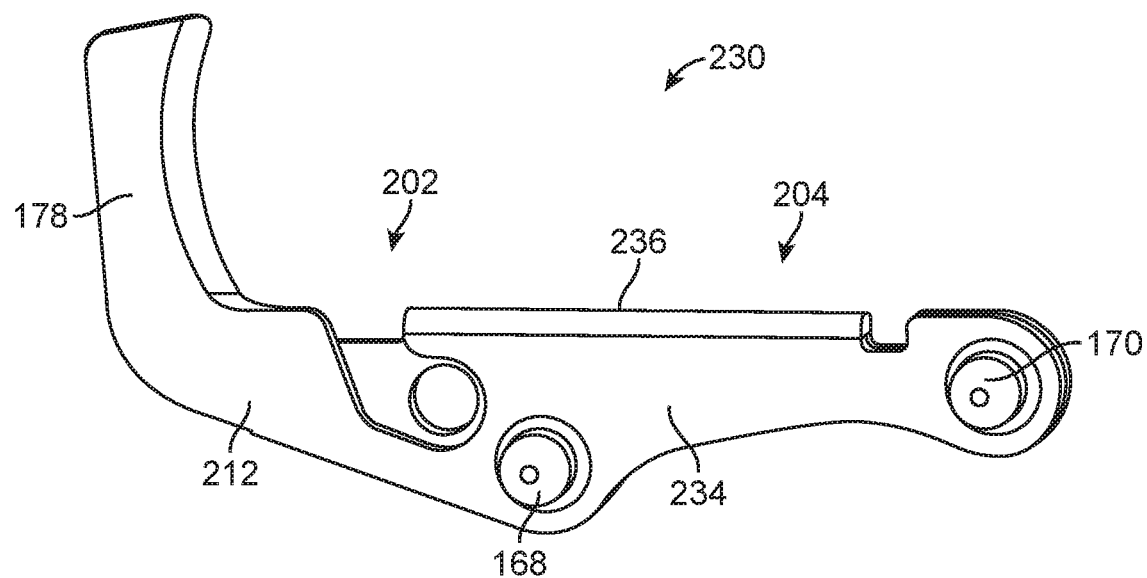

FIGS. 10A and 10B show a knife member 230 having a laminate construction in which portions of the first frame portion 202 and the second frame portion 204 are formed from first and second sheets 232,234 of metal. The knife member 230 can be formed from a metal stamping that is folded at upper bend portion 236. This can provide enhanced rigidity for coupling of the knife member 230 to the drive member 144. The knife blade 178 is formed from only the second sheet 234, as is the fused portion 212 located within the first frame portion 202. Hence, the failure mode of the fused portion 212 will bending at that location, as opposed to a fracture, to place the knife blade 178 underneath the longitudinal slot 108 and alleviate a jam.

Figure 10C:
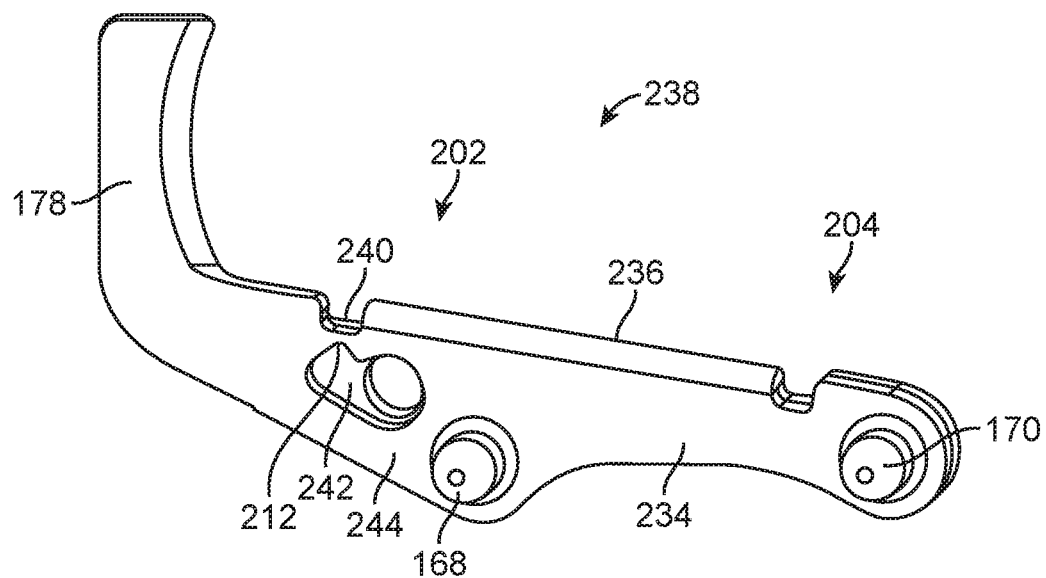

FIG. 10C shows a knife member 238 having a similar laminate construction as shown at FIGS. 10A and 10B. However, here the fused portion 212 comprises a thin portion of material between an upper notch 240 and an opening 242 of the second sheet 234. This thin portion is thinner than portions of knife member 238 on the sides of notch 240 The fused portion 212 will fracture because it has the smallest cross-sectional area of the first frame portion 202. In turn, a lower portion 244 of the first frame portion will bend and prevent the first frame portion 202 and second frame portion 204 from separating.

Figure 11A:
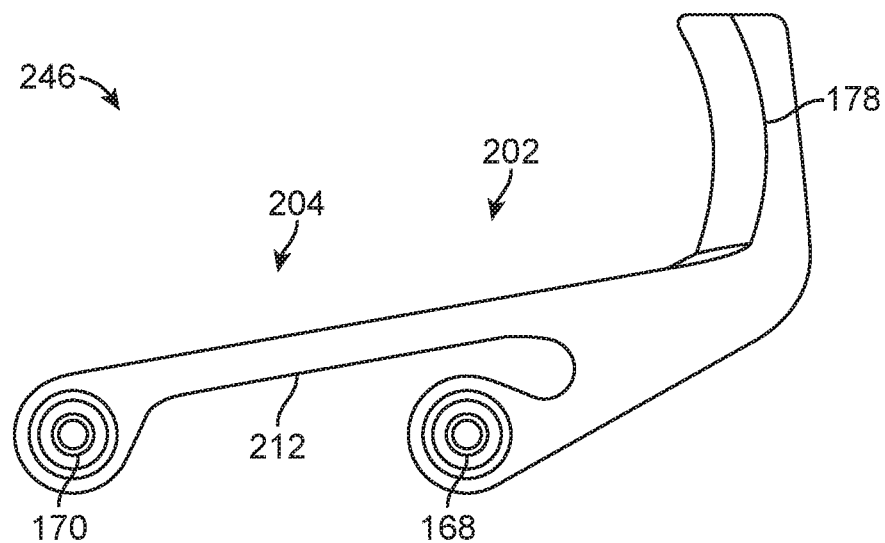
FIG. 11A shows a side views of a knife member having a mechanical fuse, in accordance with some embodiments.
Figure 11B:
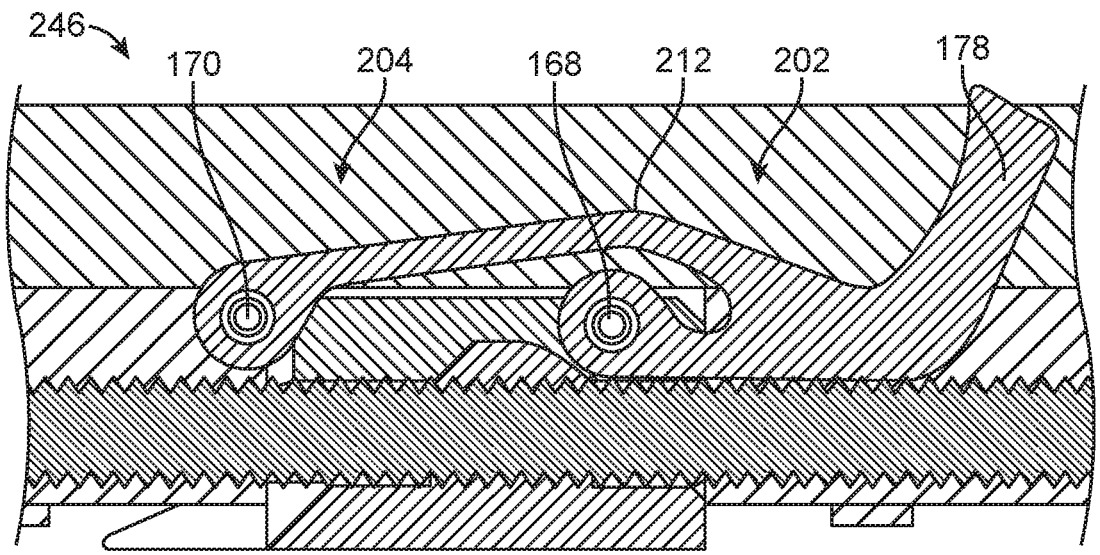
FIGS. 11B and 11C show failure modes of the knife member of FIG. 11A, in accordance with some embodiments.
Figure 11C:
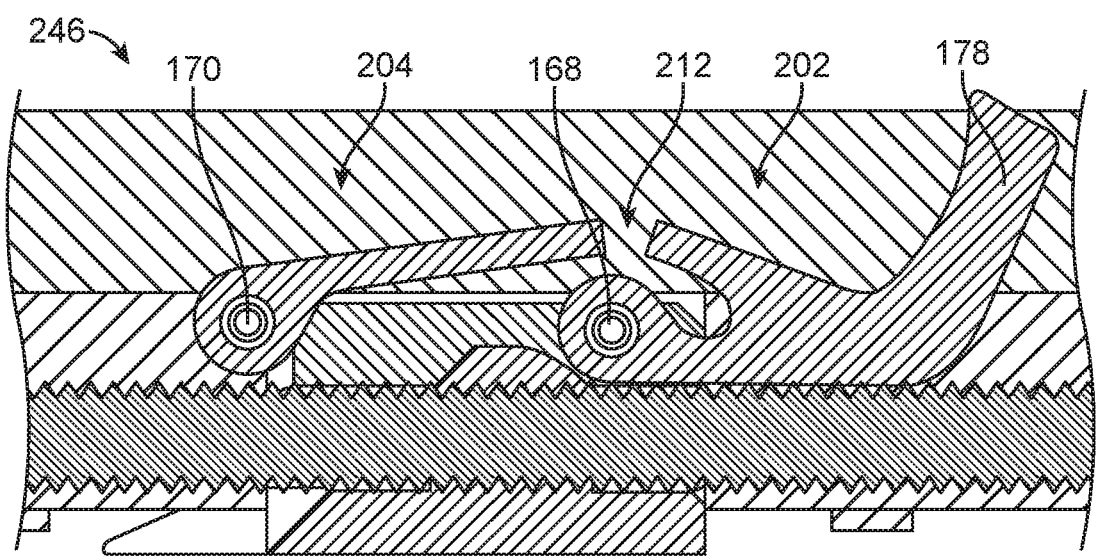

FIG. 11A shows a knife member 246 in which the fused portion 212 is an elongate portion of the second frame portion 204. The fused portion 212 has a relatively large length to width ratio and will be placed into tension when the knife blade 178 jams. Hence the fused portion is a section configured for elastic deformation such that a necking portion is formed. The necking portion can bend as it forms the smallest cross-sectional area of the second frame portion 204 to place the knife blade 178 underneath the longitudinal slot 108. This failure mode is depicted at FIG. 11B. However, in some embodiments, the fused portion 212 will eventually fracture, thereby separating the first frame portion 202 from the second frame portion 204. This failure mode is depicted at FIG. 11C.

The methods disclosed herein can be employed in any suitable application. For example, the methods disclosed herein can be employed in surgical instruments, manual or powered, hand-held or telesurgical, directly controlled or teleoperated, for open or minimally invasive (single or multi-port) procedures.

Other variations are within the spirit of the present invention. For example, while fused portions are depicted at one of the first and second frame portions, in some embodiments, both frame portions can includes fused portions. Also, although the failures of the fused portions are generally described in terms of material fracture, the fused portions of some embodiments may fail by plastic deformation or some other type of hardware failure. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical knife member comprising:
   a blade portion for operation within a surgical stapling device;
   a first frame portion extending from the blade portion to a first connection portion that is movably connectable to the surgical stapling device; and
   a second frame portion extending from the first frame portion to a second connection portion that is movably connectable to the surgical stapling device,
   wherein a fused frame portion selected from the group consisting of the first frame portion and second frame portion comprises a fused portion that fails when a predetermined amount of force is applied to the fused portion.

2. The surgical knife member of claim 1, wherein the fused portion comprises a notched portion.

3. The surgical knife member of claim 1, wherein the fused portion comprises a thinner seclection that is thinner relative to the remainder of the fused frame portion.

4. The surgical knife member of claim 1, wherein the fused portion fails by fracturing when the predetermined amount of force is applied to the fused portion.

5. The surgical knife member of claim 1, wherein the fused portion fails by bending when the predetermined amount of force is applied to the fused portion.

6. The surgical knife member of claim 1, wherein the fused frame portion comprises an opening proximate to the fused portion.

7. The surgical knife member of claim 1, wherein:
   the fused frame portion comprises a first strut and a second strut;
   the first strut is separated from the second strut by an opening; and the fused portion comprises a notched portion in the first strut.

8. The surgical knife member of claim 1, wherein:
the fused frame portion comprises the first frame portion; and
the second frame portion comprises an elongated strut that elastically deforms toward the fused portion in response to the predetermined amount of force being applied to the fused portion.

9. The surgical knife member of claim 1, wherein:
the first frame portion comprises a laminated construction comprising a first sheet of material and a second sheet of material; and
the blade portion and the fused portion are portions of the second sheet of material.

10. A surgical stapling cartridge assembly comprising:
a cartridge that is removably attachable to a jaw of an end effector of a surgery tool, the cartridge comprising plurality of staples arranged along a slot;
a drive member that is drivable along the slot; and
a knife member that is carried by the drive member, the knife member having a blade portion that extends above the slot, wherein the knife member comprises a fused portion that fails and recedes the blade portion beneath the slot when a predetermined amount of force is applied to the fused portion.

11. The surgical stapling cartridge assembly of claim 10, wherein the knife member comprises:
a first frame portion extending from the blade portion to a first connection portion that is moveably connectable to the drive member;
a second frame portion extending from the first frame portion to a second connection portion, the second connection portion for moveable connection that is moveably connectable to the drive member,
wherein at least one frame portion selected from the group consisting of the first frame portion and the second frame portion comprises the fused portion.

12. The surgical stapling cartridge assembly of claim 11, wherein the fused portion comprises a notched portion.

13. The surgical stapling cartridge assembly of claim 11, wherein the fused portion comprises a relatively thin section relative to the remainder of the at least one frame portion.

14. The surgical stapling cartridge assembly of claim 11, wherein the fused portion fails by fracturing when the predetermined amount of force is applied to the fused portion.

15. The surgical stapling cartridge of claim 11, wherein the fused portion fails by bending when the predetermined amount of force is applied to the fused portion.

16. The surgical stapling cartridge assembly of claim 11, wherein the at least one first frame portion comprises an opening proximate to the fused portion.

17. The surgical stapling cartridge of claim 11, wherein:
the at least one frame portion comprises a first strut and a second strut that is separated from the first strut by an opening; and
the fused portion comprises a notched portion of the first strut.

18. The surgical stapling cartridge of claim 11, wherein:
the at least one frame portion comprises the first frame portion; and
the second frame portion comprises an elongated strut that elastically deforms into the fused portion when the predetermined amount of force is applied to the fused portion.

19. The surgical stapling cartridge assembly of claim 11, wherein;
the first frame portion and the second frame portion comprise a laminated construction comprising a first sheet and a second sheet; and
the blade portion and the fused portion are located on the second sheet.

20. A surgical knife member comprising:
a blade portion for operation within a surgical stapling device;
a first frame portion extending from the blade portion to a first connection portion that is movably connectable to the surgical stapling device; and
a second frame portion extending from the first frame portion to a second connection portion, that is movably connectable to the surgical stapling device,
wherein a fused frame portion selected from the group consisting of the first frame portion and second frame portion comprises a fused portion, the fused portion comprising a notched portion and fails by fracturing in response to a predetermined amount of force is applied to the surgical knife member.

21. The surgical knife member of claim 20, wherein the fused frame portion is the first frame portion, the first frame portion comprises a first strut and a second strut separated from the first strut by an opening, the first strut comprises the notched portion, and the second frame portion comprises an elongated strut configured to elastically deform toward the fused portion in response to the predetermined amount of force.

* * * * *